US007695954B2

(12) United States Patent
Bachman et al.

(10) Patent No.: US 7,695,954 B2
(45) Date of Patent: Apr. 13, 2010

(54) MICROPATTERNED PLATE WITH MICRO-PALLETS FOR ADDRESSABLE BIOCHEMICAL ANALYSIS

(75) Inventors: Mark Bachman, Irvine, CA (US); Guann-Pyng Li, Irvine, CA (US); Nancy Allbritton, Irvine, CA (US); Christopher Sims, Irvine, CA (US)

(73) Assignee: The Regents of The University of California, Oakland, CA (US)

( * ) Notice: Subject to any disclaimer, the term of this patent is extended or adjusted under 35 U.S.C. 154(b) by 923 days.

(21) Appl. No.: 11/243,926

(22) Filed: Oct. 4, 2005

(65) Prior Publication Data

US 2006/0121500 A1 Jun. 8, 2006

Related U.S. Application Data

(63) Continuation-in-part of application No. 11/112,407, filed on Apr. 21, 2005.

(60) Provisional application No. 60/615,882, filed on Oct. 4, 2004.

(51) Int. Cl.
*C12M 1/34* (2006.01)
*C12M 3/00* (2006.01)

(52) U.S. Cl. .................................................. 435/288.4

(58) Field of Classification Search ............... 435/288.4
See application file for complete search history.

(56) References Cited

U.S. PATENT DOCUMENTS

| | | | | |
|---|---|---|---|---|
| 5,998,129 | A | 12/1999 | Schütze et al. | |
| 6,090,919 | A | 7/2000 | Cormack et al. | |
| 6,529,835 | B1 * | 3/2003 | Wada et al. | 702/21 |
| 2001/0006815 | A1 | 7/2001 | Rabbani et al. | |
| 2003/0059764 | A1 * | 3/2003 | Ravkin et al. | 435/4 |
| 2003/0129741 | A1 | 7/2003 | Ramstad | |
| 2004/0087052 | A1 | 5/2004 | Kalakis et al. | |

FOREIGN PATENT DOCUMENTS

| | | | |
|---|---|---|---|
| WO | WO 97/29355 | A | 8/1997 |
| WO | WO 02/094454 | A1 | 11/2002 |
| WO | WO 03/016868 | A | 2/2003 |
| WO | WO 03/035824 | A | 5/2003 |

(Continued)

OTHER PUBLICATIONS

Europe, EP 05 80 2866, EP Search Report, Apr. 24, 2009.

(Continued)

*Primary Examiner*—Walter D Griffin
*Assistant Examiner*—Lydia Edwards
(74) *Attorney, Agent, or Firm*—Orrick, Herrington & Sutcliffe LLP

(57) ABSTRACT

A plate manufactured to enable samples of cells, micro-organisms, proteins, DNA, biomolecules and other biological media to be positioned at specific locations or sites on the plate for the purpose of performing addressable analyses on the samples. Preferably, some or all of the sites are built from a removable material or as pallets so that a subset of the samples of interest can be readily isolated from the plate for further processing or analysis. The plate can contain structures or chemical treatments that enhance or promote the attachment and/or function of the samples, and that promote or assist in their analyses.

19 Claims, 11 Drawing Sheets

FOREIGN PATENT DOCUMENTS

| | | | |
|---|---|---|---|
| WO | WO 03/039750 | A | 5/2003 |
| WO | WO 2004/024328 | A | 3/2004 |
| WO | WO 2006041938 | A2 | 4/2006 |
| WO | WO 2006060922 | A1 | 6/2006 |

OTHER PUBLICATIONS

Europe, EP 07 79 7210, EP Search Report, Feb. 26, 2009.

Barron et al., "Laser Printing of Single Cells: Statistical Analysis, Cell Viability, and Stress," Annals of Biomedical Engineering, 33:2, pp. 121-130 (Feb. 2005).

Langer et al., "Live cell catapulting and recultivation does not change the karyotype of HCT116 tumor cells," Cancer Genetics an Cytogenetics, No. 161 pp. 174-177 (2005).

Stich et al., "Live Cell Catapulting and Recultivation," Pathology Research and Practice, 199:6, pp. 405-409 (Jan. 1, 2003).

Watson, Molecular Biology of the Gene, Third Edition, W.A. Benjamin, Inc., Menlo Park, CA, 1976, p. 62.

Zoeller et al., Strategies for Isolating Somatic Cell Mutants Defective in Liquid Biosynthesis, Methods of Enzymology, vol. 2, pp. 34-51 (1992).

* cited by examiner

MICROPATTERNED PLATE WITH MICRO-PALLETS FOR ADDRESSABLE BIOCHEMICAL ANALYSIS

CROSS-REFERENCE TO RELATED APPLICATIONS DATA

This application is a continuation-in-part of U.S. patent application Ser. No. 11/112,407, filed Apr. 21, 2005, and this application claims the benefit of U.S. provisional patent application No. 60/615,882, filed Oct. 4, 2004, which applications are incorporated herein by reference.

FIELD OF THE INVENTION

The present invention relates to biochemical analysis and, more particularly, to a micropatterned plate with micro-pallets that facilitates addressable biochemical analysis.

BACKGROUND

Conventional systems allow for biological materials to be positioned in arrays on surfaces. Material can be placed by mechanically putting materials in specific locations ("spotting"), by building cavities to collect the material (microwells), by treating the surface in specific regions, or by combinations of these methods. Most of these techniques do not work well for living cells. Once positioned, samples are almost never removed for further analysis or processing.

Adherent cells are typically analyzed by plating them on a surface then looking for them using a microscope. The locations of the cells are random so that finding the cells can be a time consuming process. To speed this up, robotic systems that utilize machine vision are sometimes used to find the cells within the field of view of the microscope image. In some cases a subset of cells are isolated by the following method: A sacrificial base layer is placed over the plate. Cells are grown on the base layer. A high powered laser is used to cut a circle around the cells of interest, through the sacrificial layer. Cells can be isolated by peeling away the sacrificial layer, or by catapulting the cut material from plate using a high powered laser pulse, carrying the cell with it.

Nonadherent cells can be analyzed quickly using a flow cytometer that rapidly flows a stream of cells past a detector apparatus. Cells of interest can be sorted by a downstream electrostatic system that moves droplets into collection containers. This method will also work for other biological media such as proteins and DNA if they can be attached to small beads. This method does not work well for larger samples (such as multi-celled organisms) and is difficult to multiplex.

SUMMARY

The present invention provides a plate manufactured in such a way that cells, micro-organisms, proteins, DNA, biomolecules and other biological media (herein called samples) can be positioned at specific locations (herein called sites) on the plate for the purpose of performing addressable analyses on the samples. Furthermore, in accordance with the present invention, some or all of the sites are built from a removable material (herein called pallets) so that a subset of the samples of interest can be readily isolated from the plate for further processing or analysis. The plate can contain structures or chemical treatments that enhance or promote the attachment and/or function of the samples, and that promote or assist in their analyses. The plate can also contain structures that aid in the coupling between the plate and external instruments. The plate can also contain additional structures that aid in accessory operations, such as maintaining proper chemical conditions for the samples.

The present invention advantageously provides (1) a plate with structures (sites) patterned on it that are intended to attach samples at known locations, (2) structures and plates that are treated or further patterned to improve the ability to perform analysis on the samples, (3) sites that are removable on demand so that laser cutting is not required, and released samples can be readily collected (4) additional micropatterned features such as structural elements, electrodes, and optical encoders that assist in the operation of the array plate, (5) placement of these sites in conventional cassettes or trays, and (6) placement of these sites in specialized cassettes or trays. As such, the present invention enables high speed, addressable analysis of biological and chemical samples, as well as an efficient method for isolating subsets of samples from a larger population of samples.

Further, objects and advantages of the invention will become apparent from the following detailed description.

DETAILED DESCRIPTION OF THE PREFERRED EMBODIMENT

Figure 1A:
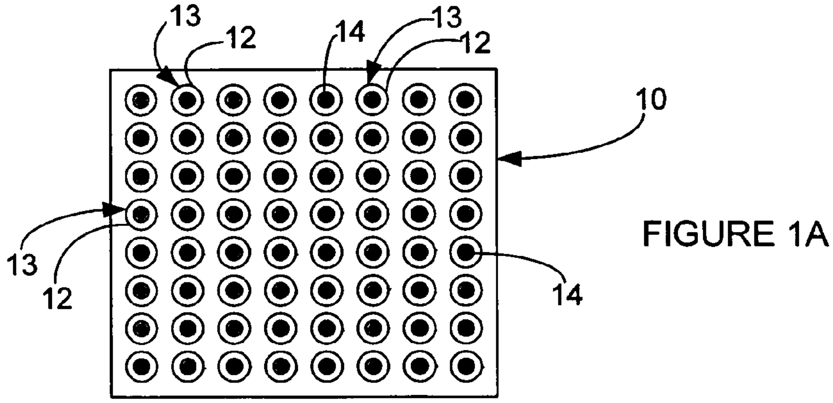
FIG. 1A is a micro-pallet plate having an array of micro-pallets.

Each of the additional features and teachings disclosed below can be utilized separately or in conjunction with other features and teachings to provide an improved micropatterned plate with micro-pallets that facilitates addressable biochemical analysis. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description can not be necessary to practice the invention in the broadest sense, and are instead taught merely to particularly describe representative examples of the present teachings.

Moreover, the various features of the representative examples and the dependent claims can be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

The present invention advantageously provides (1) a plate with structures (sites) patterned on it that are intended to attach samples at known locations, (2) structures and plates that can be treated or further pattered to improve the ability to perform analysis on the samples, (3) sites that are removable on demand so that laser cutting is not required, and wherein the released samples can be readily collected, (4) additional micropatterned features such as structural elements, electrodes, and optical encoders that assist in the operation of the array plate, (5) the placement of these sites in conventional cassettes or trays, and (6) the placement of these sites in specialized cassettes or trays. As such, the invention enables high speed, addressable analysis of biological and chemical samples, as well as an efficient method for isolating subsets of samples from a larger population of samples.

The system of the present invention advantageously provides removable regions where only one or a few samples can be attached. These regions are addressable, since their locations are known in advance. Optical encoders, electrodes, and the like enable this invention to be readily coupled to external instrumentation, enabling high speed addressable cell assays. Machines can move the plate to position any addressable site under the microscope. High magnification objectives can be used for imaging since only a single site is imaged (as opposed to a large field of many cells). For cells this enables much faster analysis than is currently available.

If the patterned system is placed within an existing tray or cassette, e.g., in a standard well-plate, then high throughput instruments can benefit from high speed cell analysis. Standard pipetting and handling equipment can be used.

The system can be used with molecules, compounds, cells, organisms and biological and chemical media that adhere to the surfaces, as well as for samples that do not. Cavities or other entrapment devices can be used to position non-adherent samples.

The system of the present invention also solves the problem of positive selection of samples. Removable pallets on an array allow one to quickly and selectively remove samples from the plate for further processing. The use of removable pallets eliminates the need to cut around the sample, greatly increasing the speed and throughput while reducing the complexity for selecting samples. Since the pallets are arranged on a plate, high speed analysis and sample selection can be performed at rates comparable to flow cytometry in a far simpler manner.

As depicted in FIG. 1A, the present invention fundamentally provides a plate 10 with an array of removable sites 13 (called pallets 12). In preferred embodiments, the plate 10 or pallets 12 include modifications that further enhance the operation of the plate and pallets.

In preferred embodiments, the plate 10 is manufactured in such a way that cells, micro-organisms, proteins, DNA, biomolecules and other biological media (herein called samples) can be positioned at specific locations (herein called sites 13) on the plate 10 for the purpose of performing addressable analyses on the samples 14. Furthermore, some or all of the sites 13 are preferably built from a removable material (herein called pallets 12) so that a subset of the samples 14 of interest can be readily isolated from the plate 10 for further processing or analysis. The plate can contain structures or chemical treatments that enhance or promote the attachment and/or function of the samples 14, and that promote or assist in their analyses. The plate 10 can also contain structures that aid in the coupling between the plate 10 and external instruments. The plate 10 can also contain additional structures that aid in accessory operations, such as maintaining proper chemical conditions for the samples.

Figure 1B:
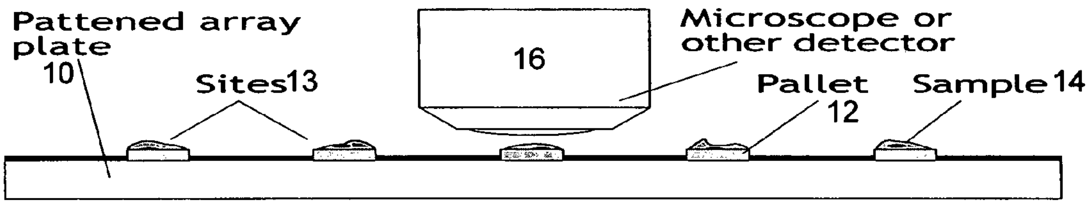
FIG. 1B is a side view of a micro-patterned plate with samples (cells) attached to pallets specific addressable sites.

Referring to FIG. 1B, the micro-patterned plate 10, as depicted, includes samples (cells) 14 attached to specific addressable sites, i.e., the pallets 12. In this embodiment, a microscope 16 of other detectors is used to image the samples 14 as the samples 14 are rapidly moved into position under the detector 16. Other detection schemes can be employed. The samples are attached to small, thin pallets 12 which adhere to the plate 10 at the sites 13. The use of pallets 12 is optional but beneficial for isolating single samples of interest. The pallet 12 can be removed at a later time to allow the experimenter to isolate samples of interest.

As depicted in FIG. 1A, the plate 10 has an array of sites 13 prepared on its surface having properties that preferably differ from the bulk material of the plate 10. The sites 13 are regions intended to be small enough to enable the entrapment of a few or single cells, micro-organisms, biomolecules or other biological or chemical media (herein called samples 14) at each site 13.

The sites 13 can be constructed of a second material (herein called pallets 12) which can be removed from the supporting plate 10, carrying the sample 14 with it. The pallets 12 can be removed by a variety of mechanisms so that samples 14 can be isolated and removed from the plate 10 by removing their supporting pallet 12. The sites 13 can be prepared by locally modifying the surface chemistry or by physically altering the surface. The plate 10 allows for single samples 14, or small numbers of samples 14, to be collected at each site 13. Each site 13 can then be imaged, or probed with light or other energy (e.g., magnetic, electrical, mechanical, thermal energy) to determine the properties of the samples 14 trapped at the site 13 or to modify the sample 14 at the site 13. Furthermore, the sites 13 containing samples 14 of interest can be removed from the plate 10 for isolation from the plate 10 for further analysis or processing. The pallets 12 can also contain structures that assist in the movement or placement of the pallets 12 after removal from the plate 10.

A pallet 12 can be removed by any means appropriate. Example methods include mechanically pushing or lifting the pallet 12 from the plate 10, using localized heat or light to change the adhesion property of the pallet 12, using acoustical or mechanical shock to dislodge the pallet 12 from the plate 10, using high energy laser pulses to dislodge the pallet 12 from the plate 10, changing the electrical or magnetic properties of the pallet 12, and the like.

Figure 2:
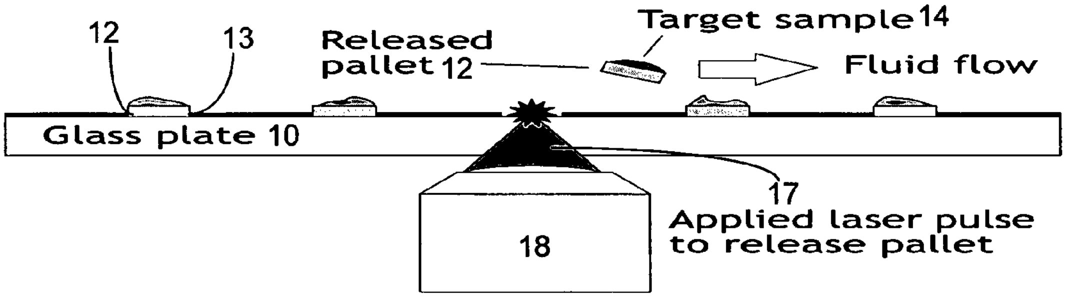
FIG. 2 is a side view of another embodiment of a micro-patterned plate and illustrates a positive selection of a sample by releasing the pallet containing the sample from the plate.

Turning to FIG. 2, an example of pallet removal using a laser pulse 17 from a laser 18 is shown. As illustrated, a positive selection of a sample 14 is accomplished by releasing the pallet 12 containing the sample 14 from the plate 10. As noted above, other methods of pallet release can be employed including the application of mechanical, electrical, thermal, optical, magnetic energy. The released pallet 12 can be flowed downstream for collection, or can be collected by other means (such as decanting or pipetting).

The sites 13 are preferably formed close together so that the plate 10 can be moved under an analysis instrument to rapidly perform analysis of many sites 13. For example, if the sites 13 are positioned 0.1 mm apart, then the plate 10 can be moved at 50 mm/sec to analyze 500 samples per second. Samples 14 can be attached to the sites 13 in any of a various number of methods. For example, living cells can be allowed to float in a medium until they attach to the sites. The remaining cells can be washed away leaving an addressable array of cells that can be rapidly imaged. Conventional methods such as spotting, silkscreening, stenciling, lithography, optical manipulation, or mechanical attachment can also be used to attach the samples to the sites.

The sites 13 can form rectangular or other regular patterns (e.g., hexagonal, circular, linear, etc.), or can be randomly oriented. The patterned sites can be positioned within a larger structure such as at the bottom of a multi-well plate. The patterned plate can allow other structures to be placed within it to facilitate other functions, for example the use of temporary dividers that allow different samples to be introduced into different regions of the plate, or fluidic structures (e.g., channels) to facilitate the flow of buffer across the sites (as illustrated in FIG. 3).

Figure 3:
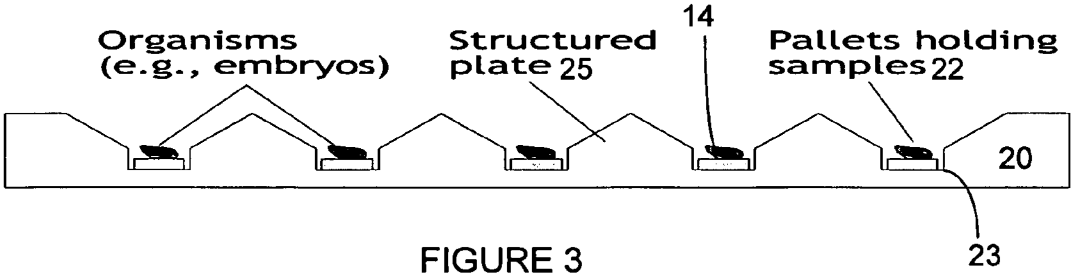
FIG. 3 is a side view of another embodiment of a micro-patterned plate with samples (organisms) attached to specific addressable sites.

Referring to FIG. 3, a micro-patterned plate 20 is shown with samples 24 (organisms) attached to specific addressable sites 23. In this embodiment, a 3-D structured pattern 25 on the plate 20 assists in the collection of the sample 24 at the specific sites, where they can be attached directly to the plate 20 or to small pallets 22 at each site 23.

The physical shape of the surface can be modified to enhance the capture at sites (and not at non-sites), or to improve the analysis. For example, the sites (see 33, FIG. 4) can be formed on top of posts. This provides the advantage that non-sites are out of focus (see 35, FIG. 4) for a microscopy imaging system, reducing background in the image. Other examples can include cavities that trap samples within them, or opaque regions on the plate.

Other features can be added to the plate to facilitate its coupling to an external instrument. For example, optical encoders, electrodes, or magnetic devices can be included on the plate to facilitate placement; sensors can be used to test for growth conditions, fiducial marks can be included for optical alignment, etc.

Figure 4:
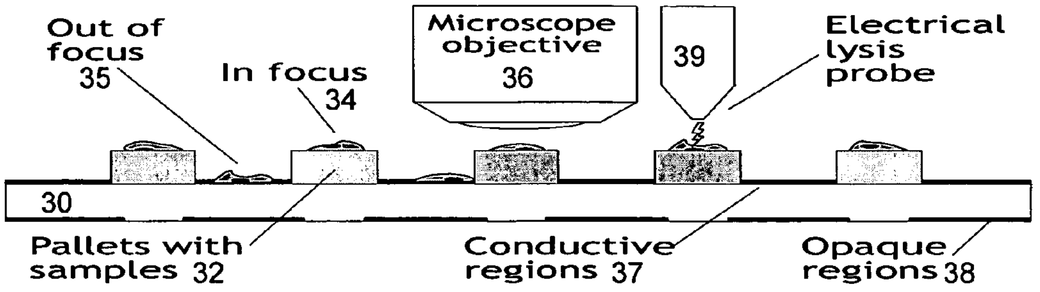
FIG. 4 is a side view of another embodiment of a micro-patterned plate with samples (cells) attached to specific addressable sites.

Some of the noted enhancements are shown in FIG. 4. As depicted in FIG. 4. a micro-patterned plate 30 includes samples (cells) 34 attached to pallets 32 or posts at specific addressable sites 33. In this embodiment, a microscope objective 36 is used to image the "in focus" samples 34 as they are rapidly moved into position under the objective 36. Other included features include patterned electrodes 37, patterned opaque regions 38, and externally applied electrical fields 39 that can be used to lyse specific cells of interest.

The chemical property of the sites can also be modified to enhance the capture at the sites (and not at non-sites), or to improve the analysis. For example, surface chemistry can be modified to make some regions hydrophobic and other hydrophilic to enhance cell adhesion at the hydrophobic sites. Surface chemistry can also be used to make a non-site of the plate opaque and site-regions transparent to provide local apertures for enhanced optical imaging.

The array of sites can be produced within existing industry standard trays and cassettes. For example, the sites can be fabricated within the bottoms of multi-well plates, providing high speed addressable assays to industry standard equipment (see, e.g., FIG. 5). The array of sites can also be produced within a customized system of cartridges. An example of a customized cartridge is shown in FIG. 6.

Figure 5:
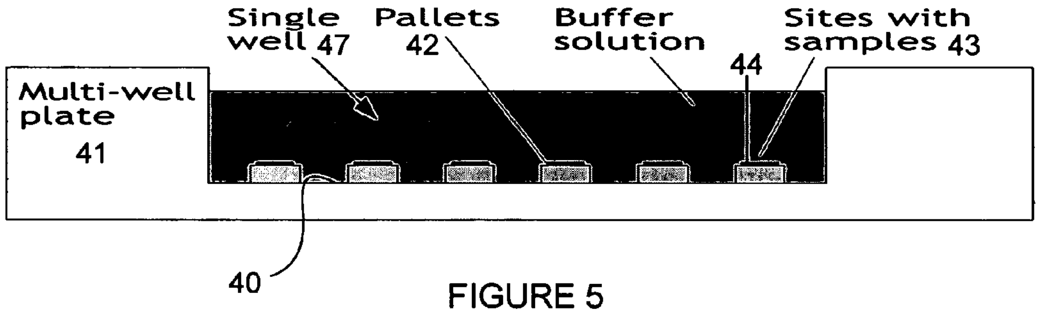
FIG. 5 is a side view of another embodiment of a micro-patterned plate placed at the bottom of a single well of a multiwell plate, allowing conventional tools to be used with the plate.

As depicted in FIG. 5, a micro-patterned plate 40 is placed at the bottom of a single well 47 of a multiwell plate 41, allowing conventional tools to be used with the plate 40. The micropatterned plate 40 includes a plurality of pallets 42 forming a plurality of sites 43 with samples 44. A buffer solution fills the single well.

Figure 6:
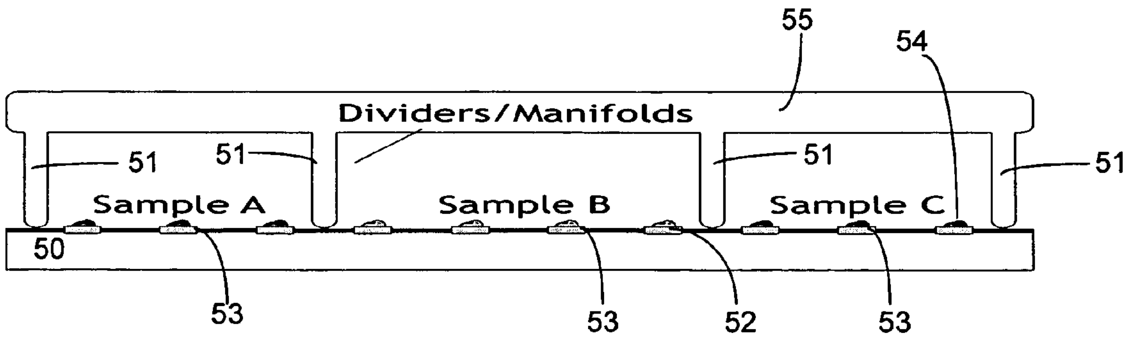
FIG. 6 is a side view of a plate showing the use of temporary or permanent dividers to allow samples of different types or histories to be plated on the plate at different locations or within different channels.

As depicted in FIG. 6, a micro-patterned plate 50 is shown to include temporary or permanent dividers 51 attached to a fluidic cap 55 to allow samples 54 of different types or histories to be plated on the plate 50 at different locations. This allows multiplexed analysis to be done on a single plate. The dividing structures 51 can also facilitate the flow of buffers over the sample regions for extraction of released pallets 52.

Figure 7A:
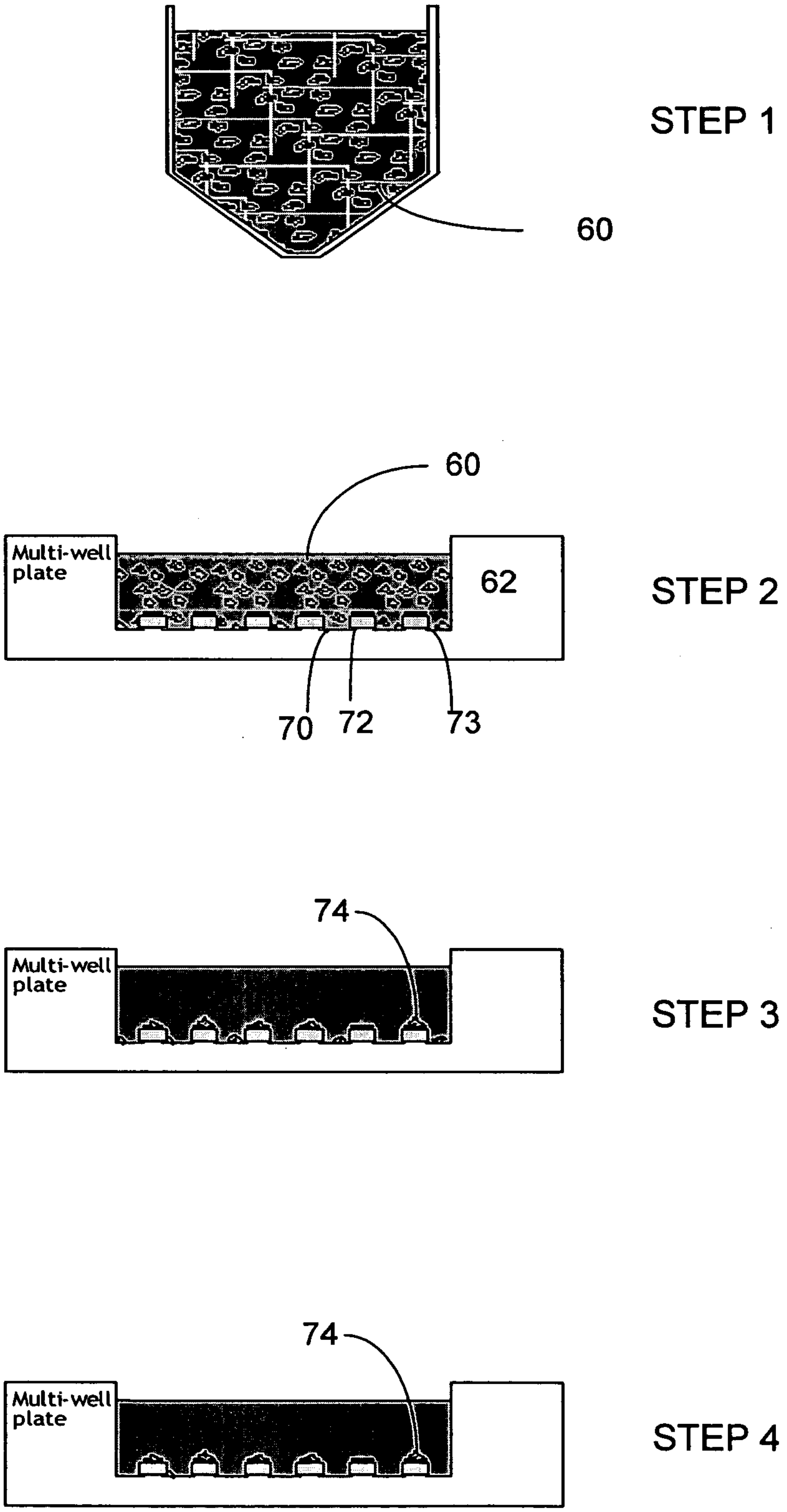
FIGS. 7A and 7B show steps in a process using a pallet plate for adherent cell screening and culturing.
Figure 7B:
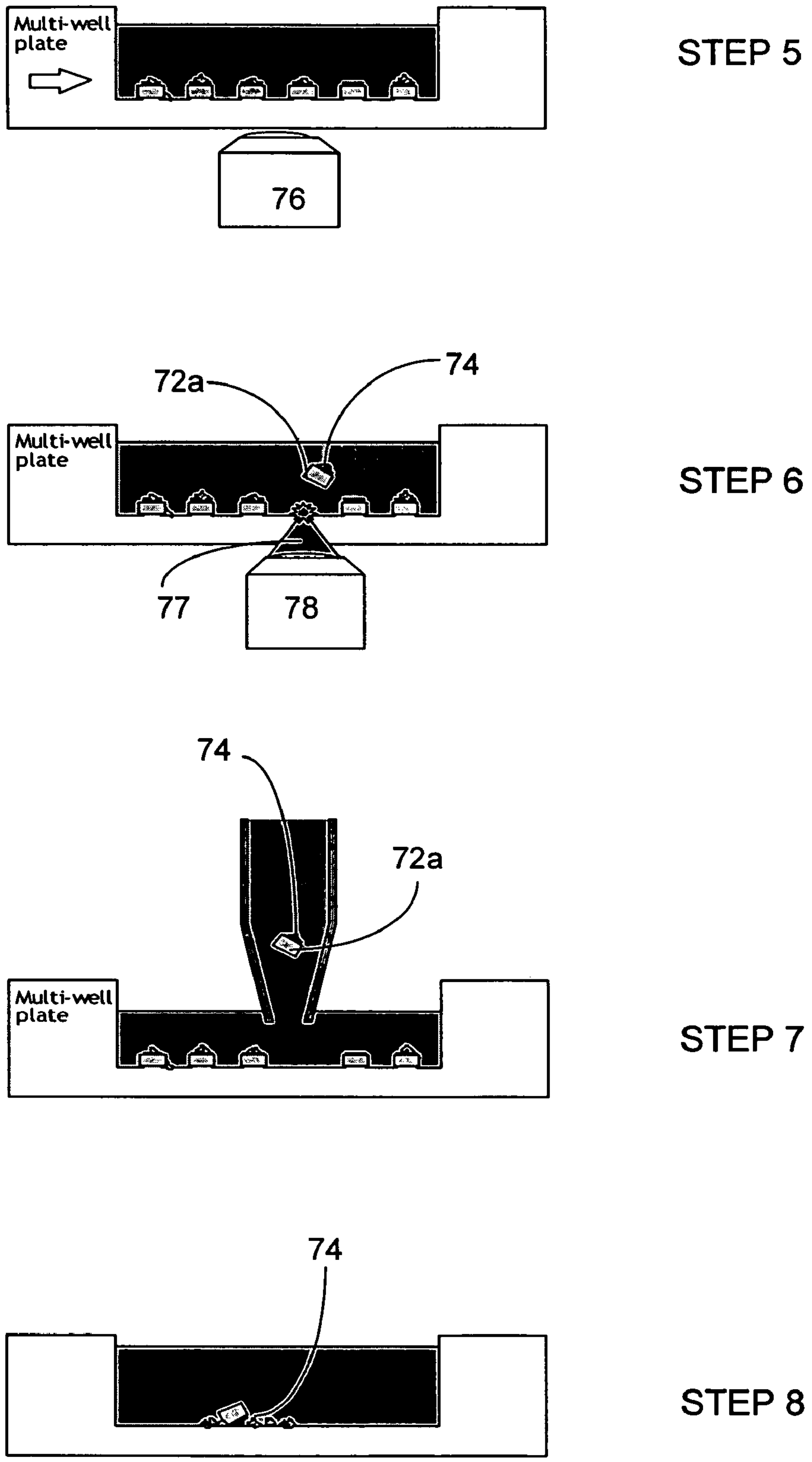

Turning to FIGS. 7A and 7B, steps in a process using a pallet plate for adherent cell screening and culturing are shown. This example illustrates how the disclosed system can be used to screen for rare cells from a large collection of cells. For example, the adherent cells can be taken from a patient biopsy and the disclosed system can be used to search for and select cells that show unusual or malignant behavior. Or adherent cells might be treated with a DNA vector in hopes of transfecting the cells, and the system used to find and isolate the cells that were properly transfected.

In accordance with the example process, cells 60 are pretreated, at step 1, according to an appropriate protocol, the cells 60 are then dispersed, at step 2, over the plate 70 and allowed to attach to the plate 70 or the pallet 72 at a plurality of sites 73. This can be done in a multiwell plate 62, as shown, or a single well plate. The cells adhere, as a sample 74, at step 3, to the plate 70 or pallet 72. Since the plate is treated and patterned, cells prefer to adhere at specific sites. At step 4, the plate is then preferably washed and further assay work is preferably performed to label the cells of interest. The plate is screened by detector 76, at step 5, to gain statistical information about the cell population and to identify cells of interest. Pallets 72*a* containing the cells of interest are (sample 74) dislodged (released), at step 6, from the plate, preferably, e.g., by a high energy laser pulse 77 from a laser 78. The free floating pallets 72*a* are then collected, at step 7, from the buffer solution. At step 8, new cell cultures are grown from the released cells 74.

Figure 8A:
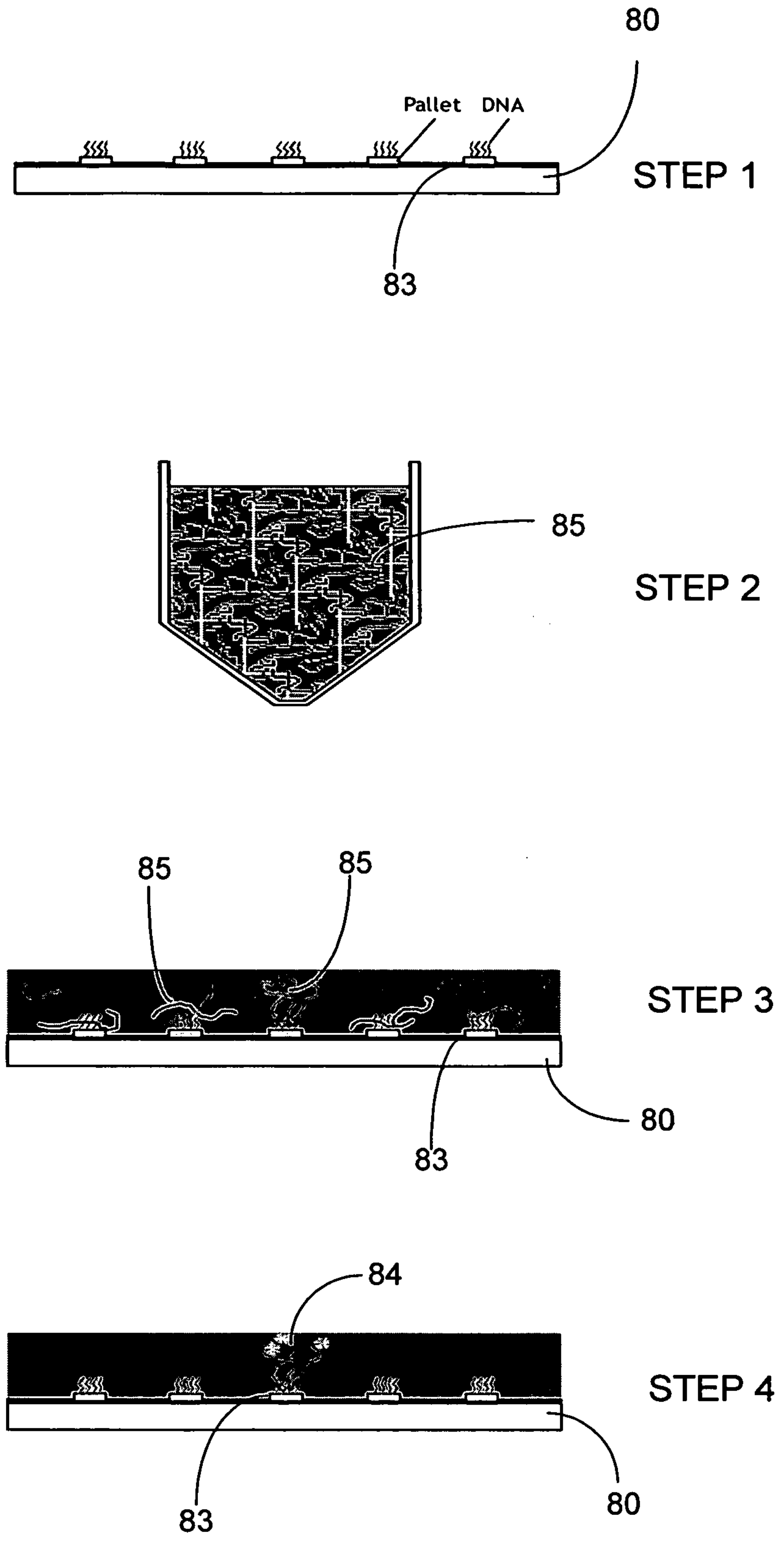
FIGS. 8A and 8B show steps in a process using a pallet plate for DNA screening.
Figure 8B:
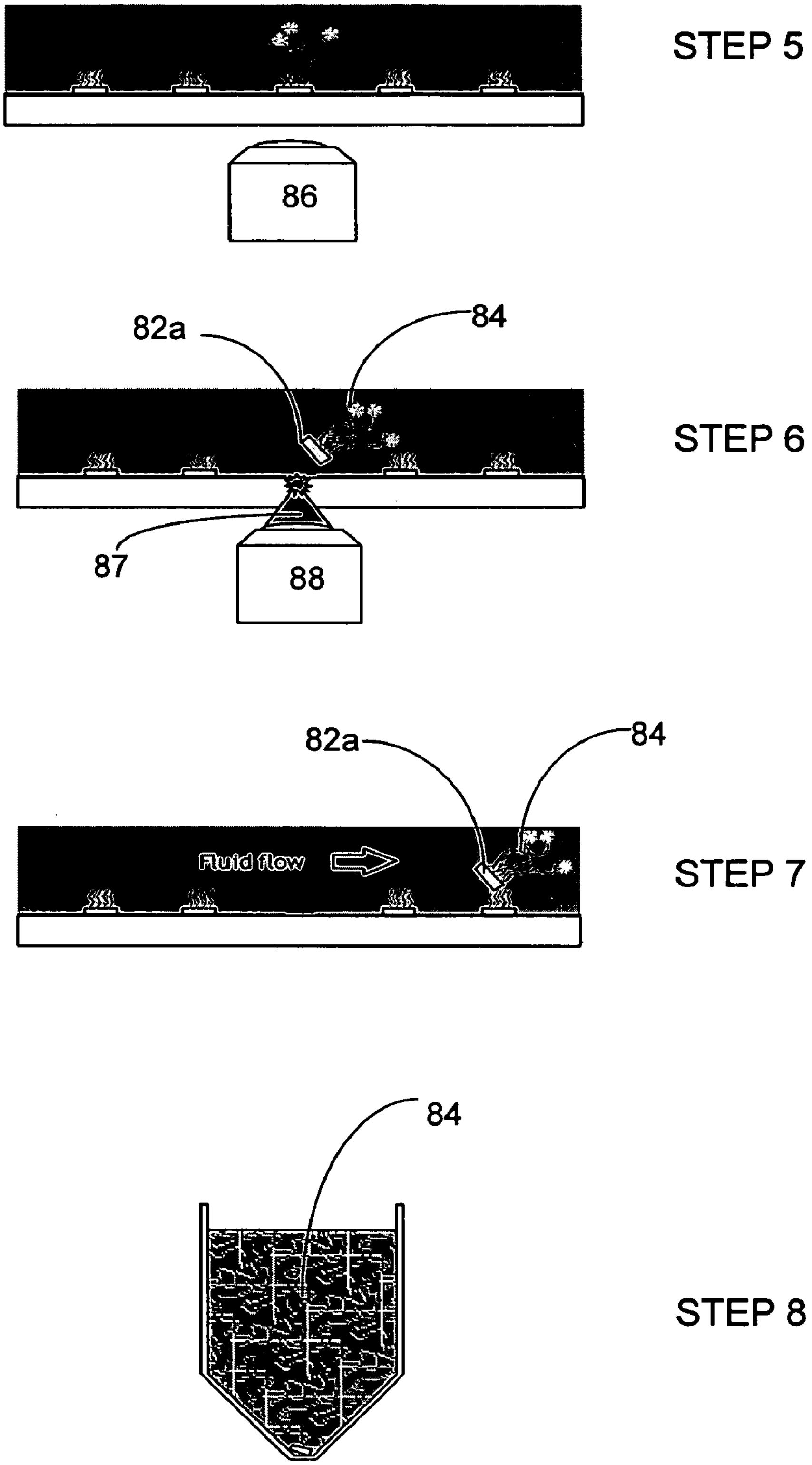

Turning now to FIGS. 8A and 8B, steps in a process using a pallet plate for DNA screening are shown. This example illustrates how the disclosed system can be used to screen for rare DNA strands from a large collection of DNA. For example, an unknown disease causing agent can be screened against a DNA plate to select strands of interest. Then the strands of interest can be isolated and PCR performed to amplify them for further analysis. The steps of the process are as follows: At step 1, a plate 80 is spotted with oligonucleotides at specific sites 83 which act as targets for DNA strands. The oligos are also prepared to act as controls. At step 2, DNA 85 is taken from sample, denatured and pretreated according to an appropriate protocol. At step 3, DNA 85 is dispersed over the plate 80 and allowed to hybridize to their matching targets at specific sites 83. At step 4, the plate is thoroughly washed to remove unbound DNA. Further assay work is performed to label the DNA of interest. The plate is then screened by the detector 86, at step 5, for statistical analysis of the sample and to identify DNA of interest. The pallets 82*a* containing the DNA of interest 84 are dislodged (released), at step 6, from the plate 80 by a high energy laser pulse 87 from a laser 88. At step 7, the free floating pallets are collected from the buffer solution. At step 8, DNA 84 is denatured from the pallet and used in PCR reaction to amplify the sample.

Figure 9:
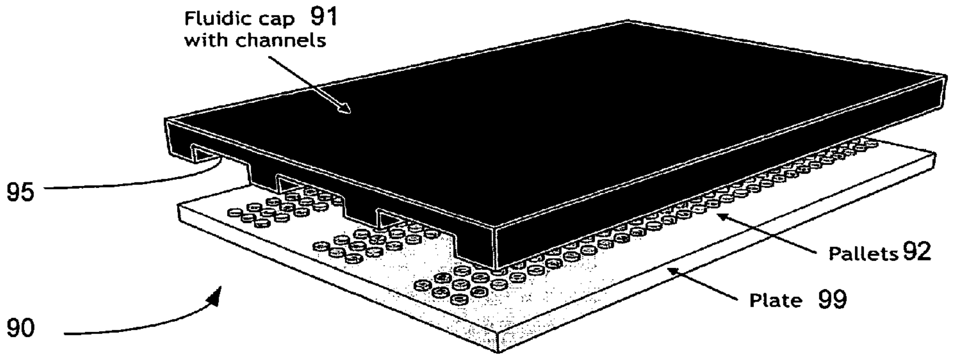
FIG. 9 is a perspective view of an integrated pallet plate cassette for automated assays.
Figure 11:
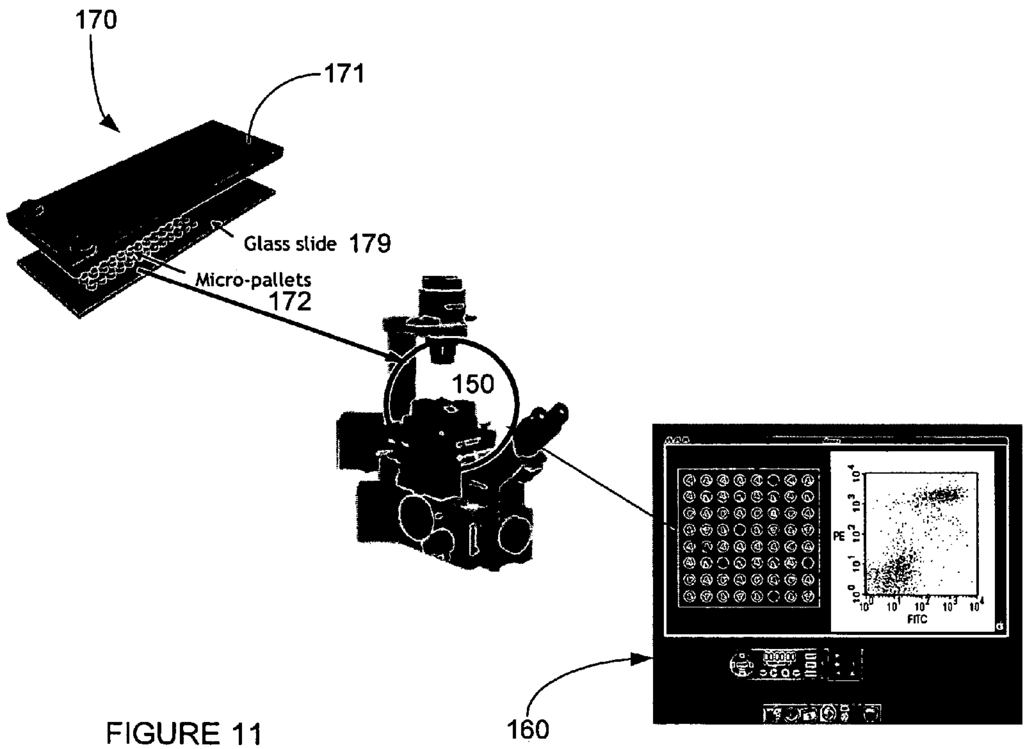
FIG. 11 is a schematic of a high content screening and cell selection system utilizing a micro-pallet cassette comprising an array of micro-pallets.

Referring to FIG. 9, an integrated pallet plate cassette 90 for automated assays is illustrated. This example illustrates how the disclosed system can be integrated into other systems to produce an automated cartridge system. As depicted in FIG. 9, the integrated pallet plate cassette 90 includes a micropallet plate 99 with a plurality of pallets 92 formed in three arrays on the plate 99, and a fluidic cap 91 with small channels 95 formed on its underside. The cap 91 mates with the micropallet plate 99 to flow buffers over the pallets 92.

Turning to FIGS. 10A through M, a process using a micromachined integrated pallet plate cassette 100 is shown. The cassette 100 includes a pallet plate 109 that preferably includes a pre-set array of releasable pallets 102 for cell culturing that are releasably positioned atop of the plate 109 formed of glass or the like. The pallets 102 are preferably treated to promote cell growth at the center of the pallets 102. The pallets 102 are preferably indexed, e.g., bar coded, so that their positions are known in advance of use of the cassette 100.

Figure 10:
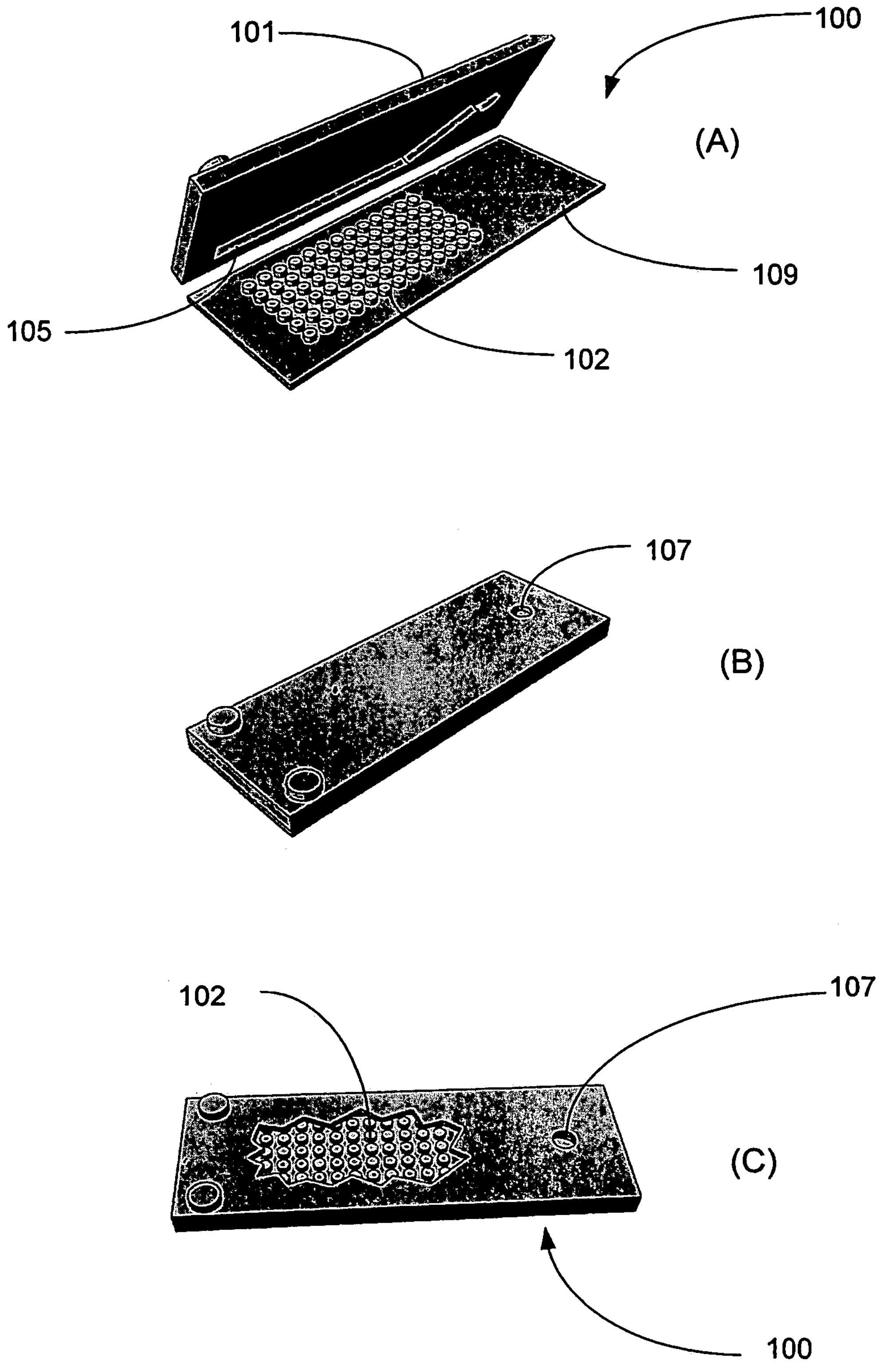
FIGS. 10A through M show steps in a process using an integrated pallet plate cassette for sample screening and culturing.
Figure 10:
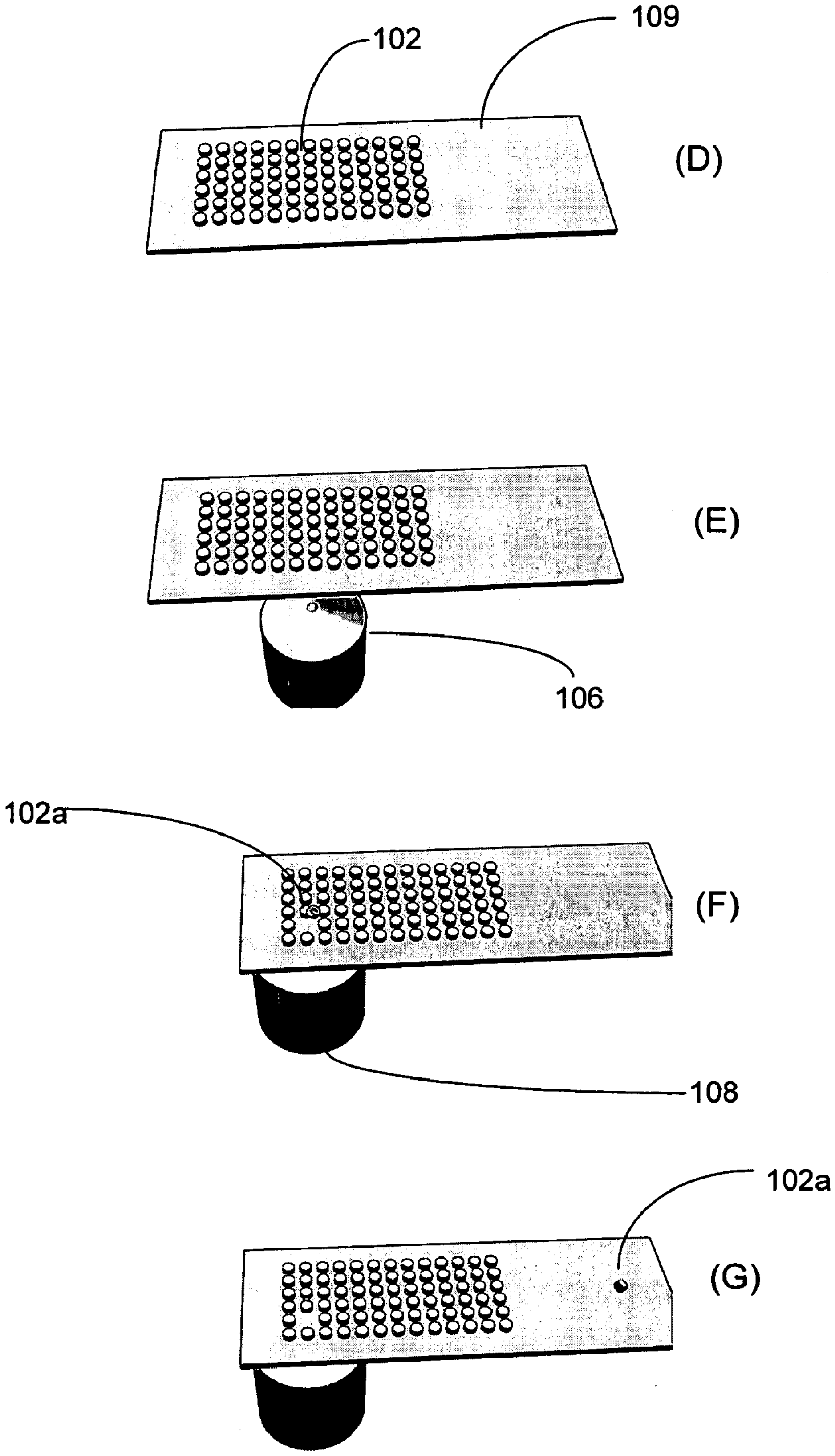
Figure 10:
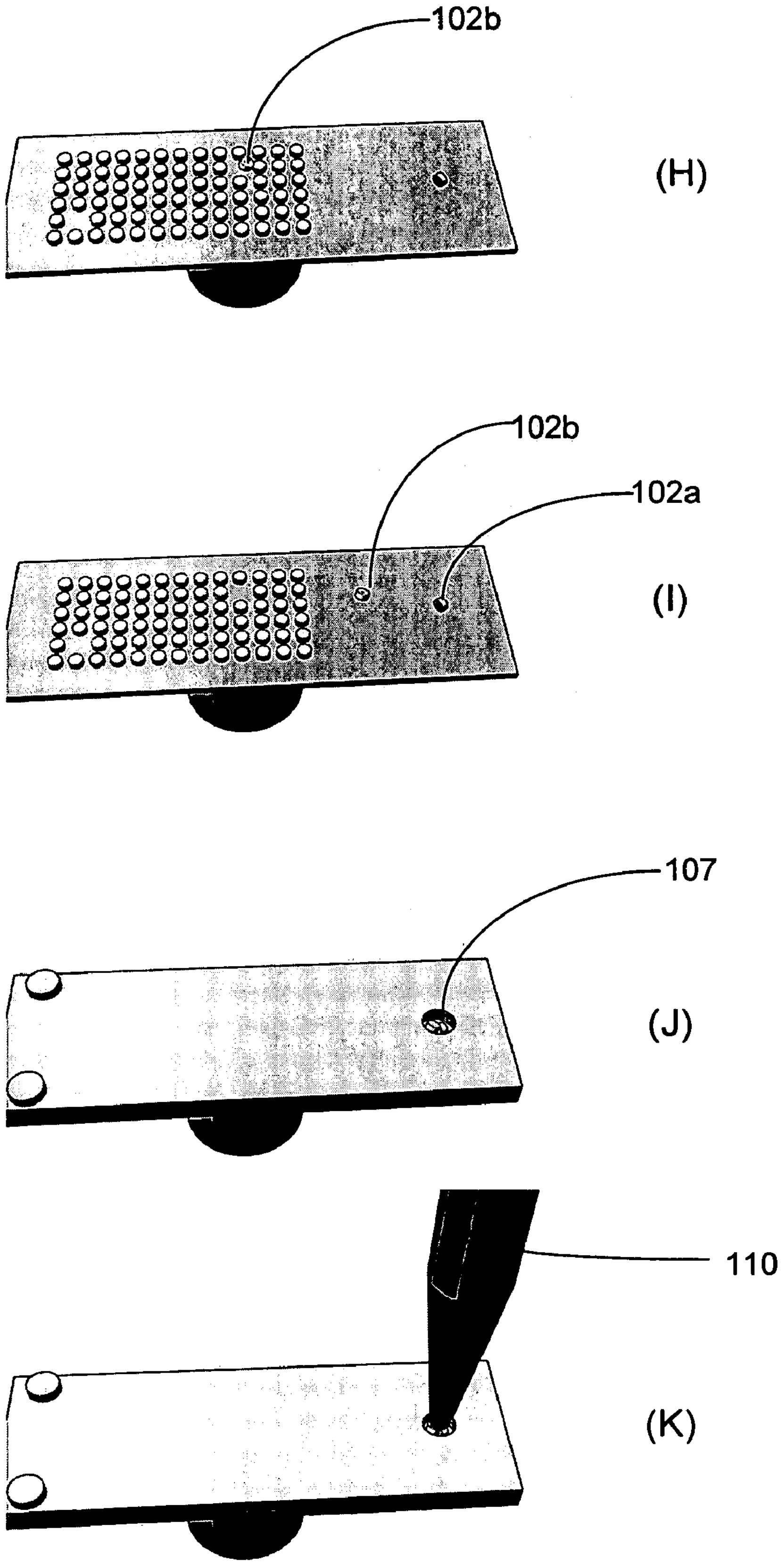
Figure 10:
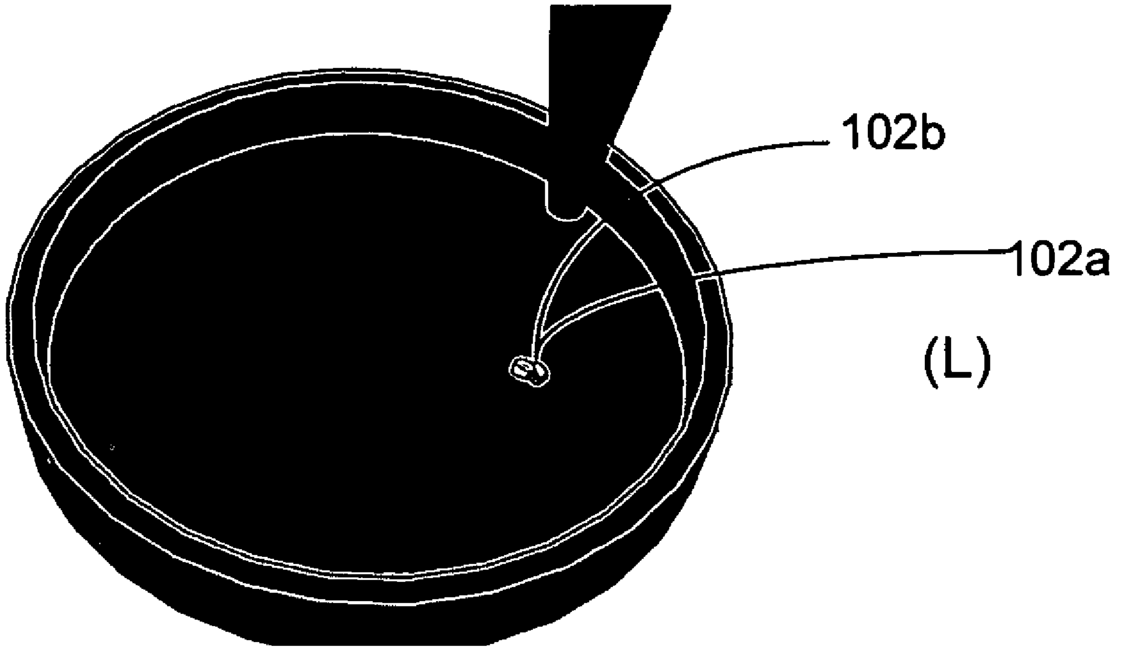
Figure 10:
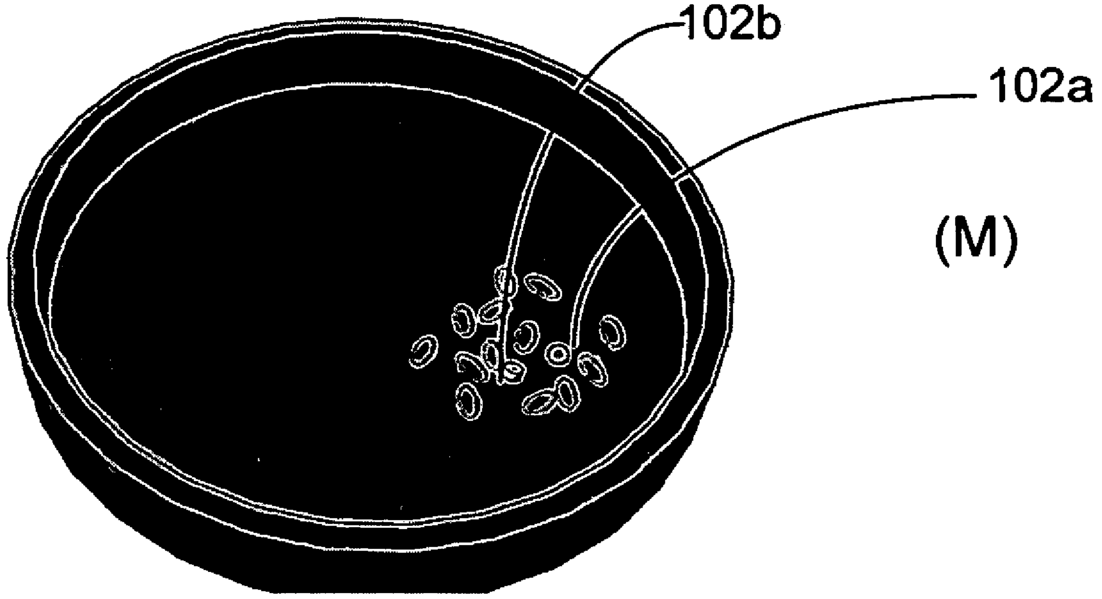

In FIGS. 10B and 10C, the cap 101 is closed on to the plate 109 revealing an access hole 107. In FIG. 10D cells are dispersed over the plate 109 and allowed to attach to the plate at specific sites 10. The plate 109 is then screened by the detector 106, as depicted in FIG. 10E, for statistical analysis of the sample and to identify cells of interest. A pallet 102*a* containing the cells of interest is dislodged (released), as shown in FIG. 10F, from the plate 109 by a high energy laser pulse from a laser 108. As shown in FIG. 10G, the free floating pallet 102*a* is collected from the buffer solution toward the end of the plate 109. In FIG. 10H, a second pallet 102*b* containing additional cells of interest is dislodged (released) from the plate 109 by a high energy laser pulse from a laser 108. As shown in FIG. 10I, the free floating pallet 102*b* is collected from the buffer solution toward the end of the plate 109. As depicted in FIGS. 10J and 10K, the pallets 102*a* and 102*b* are extracted through access hole 107 using an extractor 110. New cell cultures are grown from the released cells, as shown in FIGS. 10L and 10M.

As shown in FIG. 12, a cassette 170 comprising a substrate or plate 179 formed of glass or the like and a cap 171. The plate 169 can include an array of micro-pallets 172—e.g., providing 500,000 (50×50 microns) pallet sites—positioned on the plate 179. The cassette 170 can be used with a microscope attachment 150 for imaging, fluorescent analysis, sorting, and the like. Analysis software provided on a computer 160 can be used for high content screening and cell selection. A pallet extractor can be used to extract a selected pallet from the cassette 170.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed:

1. A device for addressable biochemical analysis comprising a plate having a top surface, and an array of removable sites attached to and extending upward from the top surface of the plate, the attachment of the removable sites configured to release the removable site from the plate upon application of an energy pulse applied along the plate at the location of the removable site.

2. The device of claim 1 wherein the sites in the array of removable sites are micropallets.

3. The device of claim 1, further comprising a sample site located atop the removable site, the sample site configured to accept a living sample.

4. The device of claim 1 further comprising a cap coupled to the plate.

5. The device of claim 4 wherein the cap includes a fluid channel.

6. The device of claim 1 wherein the plate is transparent at removable site locations.

7. A device for addressable biochemical analysis comprising a plate having a surface, and an array of pallets having, one or more pallet sides, a pallet top, and a pallet bottom, the pallet bottom removably coupled to the top surface of the plate and the pallet top extending outward from the top surface of the plate, wherein removably coupled comprises a structure adhesion which is broken by application of an energy pulse applied along the plate at the location of the pallet;

a sample site on one or more pallet tops configured to accent one or more samples, the sample site having a top surface different than a surface of the one or more pallet sides and plate surface.

8. The device of claim 7 wherein the sample sites are adapted to entrap samples to be analyzed.

9. The device of claim 7 wherein the sample sites are adapted to enable attachment of samples to be analyzed.

10. The device of claim 7 wherein the plate is formed from a first material and the pallets are formed of a second material.

11. The device of claim 10 further comprising a hydrophobic layer over the surface of the plate and the one or more pallet sides.

12. The device of claim 11 wherein the plate is micropatterned to form an array of site locations on the surface of the plate.

13. The device of claim 1 wherein the energy pulse comprises an acoustical shock, a mechanical shock or a laser pulse.

14. The device of claim 7 wherein the energy pulse comprises an acoustical shock, a mechanical shock or a laser pulse.

15. A structure for addressable biochemical analysis comprising a plate having a top surface, the top surface having a first surface area, and an array of pallets comprising two or more pallets attached to and extending upward from the top surface of the plate;

wherein the nature of the attachment of the pallets to the top surface of the plate is releasable;

wherein the two or more pallets are individually releasable from the plate;

wherein after individually releasing one or more of the two or more pallets, the plate structure is intact and the first surface area remains unchanged.

16. The structure of claim 15, wherein the array comprises at least a 3 pallet by at least a 3 pallet array.

17. The structure of claim 15, wherein the nature of the attachment of the pallets is of a nature which is broken in response to a pulse of energy applied through the plate from beneath the plate.

18. The structure of claim 15, further comprising an attachment site on top of one or more pallets, the attachment site having a surface which differs from the surface of the plate and pallet.

19. The structure of claim 18, wherein the top surface of the plate and a surface of the pallet is hydrophobic and the surface of the attachment site is hydrophilic.

* * * * *